United States Patent
Kim et al.

(10) Patent No.: US 11,332,418 B2
(45) Date of Patent: May 17, 2022

(54) METHOD AND APPARATUS FOR PREPARING OLIGOMER

(71) Applicant: LG CHEM, LTD., Seoul (KR)

(72) Inventors: Eun Kyo Kim, Daejeon (KR); Mi Kyung Kim, Daejeon (KR); Joon Ho Shin, Daejeon (KR); Hye Bin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 17/281,198

(22) PCT Filed: Aug. 7, 2020

(86) PCT No.: PCT/KR2020/010469
§ 371 (c)(1),
(2) Date: Mar. 29, 2021

(87) PCT Pub. No.: WO2021/033972
PCT Pub. Date: Feb. 25, 2021

(65) Prior Publication Data
US 2021/0395165 A1     Dec. 23, 2021

(30) Foreign Application Priority Data
Aug. 21, 2019   (KR) .......................... 10-2019-0102503

(51) Int. Cl.
*C07C 2/06* (2006.01)
*B01D 3/14* (2006.01)
*B01J 19/24* (2006.01)
*C07C 7/00* (2006.01)

(52) U.S. Cl.
CPC ................ *C07C 2/06* (2013.01); *B01D 3/143* (2013.01); *B01J 19/24* (2013.01); *C07C 7/005* (2013.01); *B01J 2219/00042* (2013.01)

(58) Field of Classification Search
CPC combination set(s) only.
See application file for complete search history.

(56) References Cited

U.S. PATENT DOCUMENTS

| | | |
|---|---|---|
| 2007/0185362 A1 | 8/2007 | Lattner et al. |
| 2011/0230690 A1 | 9/2011 | Tiita et al. |
| 2013/0090508 A1 | 4/2013 | Wang et al. |

(Continued)

FOREIGN PATENT DOCUMENTS

| | | |
|---|---|---|
| JP | 4458766 B2 | 4/2010 |
| JP | 2014-177423 A | 9/2014 |
| KR | 10-2012-0123131 A | 11/2012 |

(Continued)

*Primary Examiner* — Ali Z Fadhel
(74) *Attorney, Agent, or Firm* — Dentons US LLP (57) ABSTRACT

A method and an apparatus for preparing an oligomer, the method including supplying a feed stream including a monomer to a reactor to perform an oligomerization reaction, recovering unreacted monomer, and dissolving the recovered unreacted monomer in a solvent in a monomer dissolution device and supplying a discharge stream from the monomer dissolution device to the reactor. The method and the apparatus provide reduced investment costs and improved economic feasibility as there is no need to use a refrigerant at a very low temperature or install a separate compressor to recover and reuse the unreacted monomer in an oligomer production process.

11 Claims, 2 Drawing Sheets

(56) References Cited

U.S. PATENT DOCUMENTS

2013/0102826 A1* 4/2013 Lattner .................... C07C 2/08
  585/510
2016/0207848 A1 7/2016 Stochniol et al.

FOREIGN PATENT DOCUMENTS

| KR | 10-2015-0081565 A | 7/2015 |
| KR | 10-1749542 B1 | 6/2017 |
| KR | 10-2019-0063840 A | 6/2019 |

\* cited by examiner

METHOD AND APPARATUS FOR PREPARING OLIGOMER

CROSS-REFERENCE TO RELATED APPLICATIONS

The present application is a National Stage Application of International Application No. PCT/KR2020/010469 filed on Aug. 7, 2020, which claims the benefit of and priority to Korean Patent Application No. 10-2019-0102503, filed on Aug. 21, 2019, disclosures of which are incorporated by reference in their entirety for all purposes as if fully set forth herein.

FIELD OF DISCLOSURE

The present disclosure relates to a method for preparing an oligomer and an apparatus preparing an oligomer, and more particularly, to a method for preparing an oligomer and an apparatus for preparing oligomer which efficiently recycle a monomer recovered in an oligomer production process.

BACKGROUND

An alpha-olefin is an important material which is used in comonomers, cleaning agents, lubricants, plasticizers, and the like and is commercially widely used, and in particular, 1-hexene and 1-octene are often used as a comonomer for adjusting the density of polyethylene in the production of linear low-density polyethylene (LLDPE).

The alpha-olefins such as 1-hexene and 1-octene are produced representatively by an oligomerization reaction of ethylene. The ethylene oligomerization reaction is performed by an oligomerization reaction (trimerization reaction or tetramerization reaction) of ethylene using ethylene as a reactant, and the product produced by the reaction includes unreacted ethylene as well as a multi-component hydrocarbon mixture including the desired 1-hexene and 1-octene. The product is subjected to a separation process by a distillation column, in which the unreacted ethylene is recovered and reused in the oligomerization reaction of ethylene.

The unreacted ethylene may be recovered as a gas phase or a liquid phase. In order to recover the unreacted ethylene and reuse it in the ethylene oligomerization reaction, a pressure of a recovered unreacted ethylene stream should be increased to a pressure of a reactor. Conventionally, in order to increase the pressure of the unreacted ethylene stream to the pressure of the reactor using a pump, the unreacted ethylene stream should be a liquid phase, but to this end, the unreacted ethylene stream should be cooled to −25° C. or lower using a refrigerant at a very low temperature due to a low boiling point of ethylene. Otherwise, when the unreacted ethylene is recovered as a gas phase, a compressor should be separately installed for increasing the pressure of the unreacted ethylene stream recovered for being reused in the reactor to the pressure of the reactor, As such, the conventional method of recovering unreacted ethylene to reuse it in the oligomerization reaction has problems of having high investment costs and being economically infeasible, for example, using a refrigerant at a very low temperature, separately installing a compressor, or the like.

SUMMARY

Technical Problem

In order to solve the problems described in the Background Art, an object of the present disclosure is to provide a method and an apparatus for preparing an oligomer having reduced investment costs.

That is, an object of the present disclosure is to provide a method and an apparatus for preparing an oligomer for which there is no need to use a refrigerant at a very low temperature or install a separate compressor in order to recover and reuse unreacted ethylene in an oligomerization reaction in an oligomer production process, thereby reducing investment costs and improving economic feasibility.

Technical Solution

In one general aspect, a method for preparing an oligomer includes: supplying a feed stream including a monomer to a reactor and performing an oligomerization reaction; supplying a first discharge stream from the reactor to a first separation device and supplying a second discharge stream from the reactor to a second separation device; recovering the monomer in the second separation device as an upper discharge stream; supplying the upper discharge stream including the monomer from the second separation device to a monomer dissolution device to dissolve the upper discharge stream in a solvent supplied to the monomer dissolution device; and supplying a discharge stream from the monomer dissolution device to the reactor.

In another general aspect, An apparatus for preparing oligomer includes: a reactor for oligomerizing a feed stream including a supplied monomer, supplying a first discharge stream to a first separation device, and supplying a second discharge stream to a second separation device; a first separation device for being supplied with the first discharge stream from the reactor; a second separation device for being supplied with the second discharge stream from the reactor and supplying an upper discharge stream to a monomer dissolution device; and a monomer dissolution device for dissolving the supplied upper discharge stream from the second separation device in a supplied solvent and supplying a discharge stream to the reactor.

Advantageous Effects

According to the method for preparing an oligomer and the apparatus for preparing oligomer of the present disclosure, the recovered unreacted monomer is dissolved in the solvent and supplied to the reactor, whereby there is no need for a refrigerant at a low temperature and installation of an additional compressor which were required in the conventional method of recovering unreacted monomer.

In addition, when the recovered unreacted monomer is dissolved in the solvent, the unreacted monomer may be dissolved at a relatively high temperature, and the solvent in which the unreacted monomer is dissolved is a liquid phase, and thus, the pressure of the unreacted monomer is increased to the pressure of the reactor only by using a pump and the unreacted monomer is reintroduced to the reactor, thereby reusing the unreacted monomer.

DETAILED DESCRIPTION

The terms and words used in the description and claims of the present disclosure are not to be construed limitedly as having general or dictionary meanings but are to be construed as having meanings and concepts meeting the technical ideas of the present disclosure, based on a principle that the inventors are able to appropriately define the concepts of terms in order to describe their own inventions in the best mode.

In the present invention, the term "stream" may refer to a fluid flow in a process, or may refer to a fluid itself flowing in a pipe. Specifically, the "stream" may refer to both a fluid itself flowing in a pipe connecting each apparatus and a fluid flow. In addition, the fluid may refer to a gas or a liquid.

Hereinafter, the present invention will be described in more detail for better understanding the present invention.

According to the present invention, a method for preparing an oligomer is provided. As the method for preparing an oligomer, a method for preparing an oligomer including: supplying a feed stream including a monomer to a reactor to perform an oligomerization reaction; supplying a first discharge stream from the reactor to a first separation device and supplying a second discharge stream from the reactor to a second separation device; recovering the monomer in the second separation device as an upper discharge stream; supplying the upper discharge stream including the monomer from the second separation device to a monomer dissolution device to dissolve the upper discharge stream in a solvent supplied to the monomer dissolution device; and supplying a discharge stream from the monomer dissolution device to the reactor, may be provided.

According to an exemplary embodiment of the present invention, in a step of supplying a feed stream including a monomer to a reactor to perform an oligomerization reaction, the feed stream including the monomer may be supplied to the reactor, and the oligomerization reaction of the monomer may be performed in a liquid phase in a lower portion of the reactor. The oligomerization reaction may refer to a reaction in which a monomer is oligomerized. The oligomerization may be referred to as trimerization or tetramerization depending on the number of monomers to be polymerized, and these are collectively called multimerization.

According to an exemplary embodiment of the present invention, the monomer may be ethylene and the oligomer may be an alpha-olefin. The alpha-olefin is an important material which is used in comonomers, cleaning agents, lubricants, plasticizers, and the like and is commercially widely used, and in particular, 1-hexene and 1-octene are often used as the comonomer for adjusting the density of polyethylene in the production of linear low-density polyethylene (LLDPE). The alpha-olefin such as 1-hexene and 1-octene may be produced by for example, a trimerization reaction or a tetramerization reaction of ethylene.

According to an exemplary embodiment of the present invention, a step of oligomerizing a monomer may be performed in a reactor appropriate for a continuous process, and preferably performed under a reaction system including one or more reactors selected from the group consisting of a continuous stirred tank reactor (CSTR) and a plug flow reactor (PFR).

According to an exemplary embodiment of the present invention, the oligomerization reaction of the monomer may be performed by a homogeneous liquid phase reaction, a slurry reaction having a catalyst system in a partially or entirely not dissolved form, a two-phase liquid/liquid reaction, or a bulk phase reaction or gas phase reaction in which the product acts as a main medium, in the presence or absence of a solvent, by applying the reaction system and a common contact technology. Preferably, the step of oligomerizing a monomer may be performed in the homogeneous liquid phase reaction.

According to an exemplary embodiment of the present invention, the step of performing an oligomerization reaction may be performed at a temperature of 10° C. to 180° C., 30° C. to 150° C., or 50° C. to 120° C. In addition, the step of performing oligomerization may be performed under a pressure of 15 bar to 100 bar, 20 bar to 80 bar, or 25 bar to 60 bar. When ethylene is oligomerized within the temperature range and the pressure range, a selectivity to a desired alpha-olefin may be excellent, a by-product amount may be decreased, operational efficiency of a continuous process may be increased, and the costs may be reduced.

According to an exemplary embodiment of the present invention, the feed stream including the monomer may include a gaseous monomer, a liquid monomer, and a solvent.

The gaseous monomer included in the feed stream may be supplied as, for example, a feed stream including an ethylene monomer separated from a naphtha cracking center (NCC) process as it is or after being subjected to a storage step. In addition, the gaseous monomer may include a stream recovered in the oligomer production process.

The liquid monomer supplied to the reactor as the feed stream may include a stream recovered in the oligomer production process. In addition, the liquid monomer may include a stream in which a gaseous monomer recovered in the oligomer production process is dissolved in a solvent.

The solvent included in the feed stream may refer to a solvent for dissolving the recovered gaseous monomer. In some cases, the solvent may be further supplied to the reactor as a separate feed stream in addition to the solvent for dissolving the monomer.

According to an exemplary embodiment, in a step of supplying a first discharge stream from the reactor to a first separation device and supplying a second discharge stream from the reactor to a second separation device, a common separation column may be used as the separation device.

According to the exemplary embodiment of the present invention, the first discharge stream may be a stream including the gaseous monomer. The first discharge stream is supplied to the first separation device, and the upper discharge stream including the gaseous monomer and the lower discharge stream including the liquid monomer may be supplied to the reactor. Here, the upper discharge stream from the first separation device may be mixed with the gaseous monomer stream supplied to the reactor in a mixer and supplied to the reactor, or may be separately supplied to the reactor.

According to an exemplary embodiment of the present invention, the second discharge stream may be a stream including the liquid monomer. The second stream may be supplied to the second separation device and separated into the gaseous upper discharge stream including the monomer and the liquid lower discharge stream including the solvent and the oligomer. Here, the monomer may be recovered in the oligomer production process and reused by a step of recovering the monomer in the second separation device as the upper discharge stream. The monomer is recovered as the upper discharge stream from the second separation device and the upper discharge stream from the second separation device may be supplied to the reactor after passing through the monomer dissolution device. In addition, in the lower stream from the second separation device, the solvent and the oligomer may be separated by an additional separation process, and the separated solvent may be supplied to the reactor. In addition, the separated oligomer may be separated again into a trimer and a tetramer of the monomer by an additional separation process.

According to an exemplary embodiment of the present invention, in a step of dissolving the monomer recovered in the second separation device, a refrigerant may or may not be used. As an example, in the step of dissolving the monomer recovered in the second separation device, when the refrigerant is used, one or more selected from the group consisting of brine (an aqueous ethylene glycol solution), an aqueous propyl glycol solution, and a refrigerated coolant may be used as the refrigerant. Here, the refrigerant may include 10 parts by weight to 70 parts by weight, 30 parts by weight to 60 parts by weight, or 50 parts by weight to 80 parts by weight of ethylene glycol or propyl glycol, based on a total of 100 parts by weight of the refrigerant. As another example, in the step of dissolving the monomer recovered from the second separation device, when the refrigerant is not used, a coolant may be used. This may be selected depending on the temperature required for dissolving the recovered monomer in the solvent, and depending on the content of the recovered monomer to be dissolved in the solvent, the refrigerant or the coolant which may cool the monomer to the temperature or lower at which the monomer may be dissolved, may be selected. For example, the refrigerant or the coolant which may dissolve 80 wt % to 100 wt %, 90 wt % to 100 wt %, or 95 wt % to 100 wt % of the monomer recovered from the second separation device may be selected.

According to an exemplary embodiment of the present invention, the monomer included in the upper discharge stream from the second separation device may be dissolved in the solvent supplied to the monomer dissolution device in the monomer dissolution device. Specifically, the upper discharge stream including the gaseous monomer from the second separation device may be supplied to the monomer dissolution device, and mixed with the solvent supplied to the monomer dissolution device to dissolve the gaseous monomer in the solvent. Here, the solvent may be one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene. As a specific example, the solvent may be used in combination of two or more. As a more specific example, the solvent may be a mixture of methylcyclohexane and decane. When two or more solvents are mixed and used as the solvent, in a step of mixing the solvent having a high boiling point and dissolving the monomer in the solvent, the monomer may be liquefied at a higher temperature and a dissolution rate of the monomer may be improved.

According to an exemplary embodiment of the present invention, a temperature of the solvent supplied to the monomer dissolution device may be in a range of 10° C. to 50° C., and a pressure thereof may be in a range of 10 bar to 50 bar. For example, the supply temperature of the solvent may be in a range of 10° C. to 50° C., 20° C. to 40° C., or 25° C. to 35° C., and the supply pressure thereof may be 10 bar to 50 bar, 15 bar to 45 bar, or 20 bar to 40 bar. By supplying the solvent to the monomer dissolution device in the range of temperature and pressure, the monomer may be liquefied at a relatively high temperature in the monomer dissolution device, and the pressure of the discharge stream from the monomer dissolution device may be increased to the pressure of the reactor only by use of a pump.

According to an exemplary embodiment of the present invention, the content of the solvent supplied to the monomer dissolution device may be in a range of 0.5 to 10 times, 0.8 to 5 times, or 1 to 3 times the sum of the oligomer product and the produced by-product in the second discharge stream discharged from the reactor. By supplying the solvent having the content in the range described above is supplied, the oligomer product may be efficiently produced with a similar amount of the solvent to the amount of the solvent which has been used in the conventional method for preparing an oligomer.

According to an exemplary embodiment of the present invention, a step of supplying a discharge stream from the monomer dissolution device to the reactor is included, and the discharge stream from the monomer dissolution device may be a liquid stream including the monomer dissolved in the solvent. Specifically, the upper discharge stream from the second separation device includes the gaseous monomer, and a separate compressor for increasing the pressure up to the pressure of the reactor should be installed. Otherwise, there is a method of cooling the gaseous monomer to a liquid phase to increase the pressure of the monomer to the pressure of the reactor by the pump, but in this case, a refrigerant at a very low temperature is needed for cooling the gaseous monomer to a liquid phase.

According to an exemplary embodiment of the present invention, an operating temperature of the monomer dissolution device and a temperature of the discharge stream from the monomer dissolution device may be in a range of −10° C. to 50° C. For example, the operating temperature of the monomer dissolution device and the temperature of the discharge stream from the monomer dissolution device may be in a range of −10° C. to 50° C., 0° C. to 40° C., or 5° C. to 30° C. In the conventional method for preparing an oligomer, in order to cool the recovered gaseous monomer to a liquid phase, a refrigerant at a very low temperature is used to cool the monomer to a temperature of about −25° C. or less, and thus, there was a problem of increased costs due to the use of an expensive refrigerant. However, in the method for preparing an oligomer according to the present invention, the recovered gaseous monomer is dissolved in the solvent and then supplied to the reactor, thereby solving the above problem.

According to an exemplary embodiment of the present invention, an operating pressure of the monomer dissolution device and a pressure of the discharge stream from the monomer dissolution device may be in a range of 10 bar to 45 bar. For example, the operating pressure of the monomer dissolution device and the pressure of the discharge stream from the monomer dissolution device may be in a range of 10 bar to 40 bar, 15 bar to 35 bar, or 18 bar to 30 bar. Since the discharge stream from the monomer dissolution device is a liquid phase, the pressure may be increased to the pressure of the reactor only by using the pump, and no additional device or process is required, and thus, the process may be simplified and the process costs may be reduced.

According to an exemplary embodiment of the present invention, the method for preparing an oligomer may satisfy the following General Formula 1:

$$(M2/M1) \times 100 \geq 80 \text{ weight percent(wt \%)} \quad \text{[General Formula 1]}$$

wherein M1 is a content of the monomer in the upper discharge stream from the second separation device, and M2 is a content of the monomer in the discharge stream from the monomer dissolution device. Specifically, General Formula 1 may mean a dissolution rate of the monomer dissolved in the solvent, in the discharge stream from the monomer dissolution device, when the monomer recovered as the upper discharge stream from the second separation device is dissolved in the solvent in the monomer dissolution device and discharged as the discharge stream from the monomer dissolution device. Here, the dissolution rate of the monomer dissolved in the solvent may be 80 wt % to 100 wt %, 90 wt % to 100 wt %, or 95 wt % to 100 wt %. As such, 90 wt % or more, or the entire amount of the recovered monomer is dissolved in the solvent and recovered to the reactor to have an excellent reuse rate of the monomer, thereby improving oligomer production efficiency and reducing process costs.

According to an exemplary embodiment of the present invention, the second discharge stream from the reactor is supplied to a third separation device, an upper discharge stream from the third separation device may be supplied to the reactor, and a lower discharge stream from the third separation device may be supplied to the second separation device. Specifically, the second discharge stream of a liquid phase discharged from the reactor is supplied to the third separation device before being supplied to the second separation device to perform gas-liquid separation, and then the upper discharge stream including the gaseous monomer is supplied to the reactor and the lower discharge stream including the liquid monomer may be supplied to the second separation device. As such, a separation step is added in a manner of supplying the second discharge stream from the reactor to the third separation device before supplying it to the second separation device, thereby decreasing an amount of the monomer recovered as the upper discharge stream in the second separation device. Thus, it is possible to liquefy the monomer at a higher temperature than the temperature in the case of dissolving the monomer recovered as the upper discharge stream from the second separation device in the solvent in the monomer dissolution device.

According to the present invention, an apparatus for preparing oligomer is provided. As the apparatus for preparing oligomer, An apparatus for preparing oligomer including: a reactor for oligomerizing a feed stream including a supplied monomer, supplying a first discharge stream to a first separation device, and supplying a second discharge stream to a second separation device; a first separation device for being supplied with the first discharge stream from the reactor; a second separation device for being supplied with the second discharge stream from the reactor and supplying an upper discharge stream to a monomer dissolution device; and a monomer dissolution device for dissolving the supplied upper discharge stream from the second separation device in a supplied solvent and supplying a discharge stream to the reactor, may be provided.

According to an exemplary embodiment of the present invention, the apparatus for preparing oligomer according to the present invention may be an apparatus for performing the process according to the method for preparing an oligomer described above.

According to an exemplary embodiment of the present invention, the apparatus for preparing oligomer according to the present invention may be described with reference to the following FIGS. 1 and 2. For example, the apparatus for preparing oligomer includes a reactor 100 for oligomerizing a feed stream including a supplied monomer, and in the reactor 100, a first discharge stream including a gaseous monomer may be supplied to a first separation device 200 and a second discharge stream including a liquid monomer may be supplied to a second separation device 210.

According to an exemplary embodiment of the present invention, the feed stream supplied to the reactor 100 may include the monomer and the solvent. Specifically, the feed stream may include the gaseous monomer, the liquid monomer, and the solvent. The feed stream including the gaseous monomer may include a gaseous monomer stream directly supplied to the reactor 100 and the gaseous monomer recovered as an upper discharge stream from the second separation device 200. The gaseous monomer stream directly supplied to the reactor 100 and the gaseous upper discharge stream recovered in the first separation device 200 may be separately supplied to the reactor 100, or supplied to the reactor 100 as a mixed discharge stream mixed in a mixer (not shown).

In addition, among the feed stream supplied to the reactor, a stream including the liquid monomer may include a lower discharge stream including the liquid monomer separated in the first separation device 200 and a discharge stream from the monomer dissolution device 300 in which the gaseous monomer separated in the second separation device 210 is dissolved in the solvent. Here, the upper discharge stream from the second separation device 210 may be supplied to the reactor 100 by a pump 400, after the upper discharge stream is dissolved in the solvent supplied to the monomer dissolution device 300 in the monomer dissolution device 300.

According to an exemplary embodiment of the present invention, the first separation device 200 may be supplied with the first discharge stream from the reactor 100 and separate the stream into the upper discharge stream including the gaseous monomer and the lower discharge stream including the liquid monomer. Here, the upper discharge stream and the lower discharge stream from the first separation device 200 may be supplied to the reactor 100.

According to an exemplary embodiment of the present invention, the lower discharge stream from the second separation device 210 may include an oligomer product, a by-product, and the solvent. Here, the oligomer product, the by-product, and the solvent may be separated by an additional separation apparatus (not shown), and the separated solvent may be reused in the oligomer production process. In addition, when the oligomerization reaction is performed using an ethylene monomer as the monomer, the oligomer product may include 1-hexene and 1-octene. In this case, 1-hexene and 1-octene may be separated by an additional separation device (not shown) or separated by a separate process and used.

According to an exemplary embodiment of the present invention, a third separation device 220 which is supplied with the second discharge stream from the reactor 100 and supplies the lower discharge stream to the second separation device 210 may be further included. Specifically, before the second discharge stream from the reactor 100 is supplied to the second separation device 210, the second discharge stream is subjected to gas-liquid separation once by the third separation device 220, and then an upper discharge stream from the third separation device 220 including the gaseous monomer may be supplied to the reactor 100 and a lower discharge stream from the third separation device 220 including the liquid monomer may be supplied to the second separation device 210.

Hereinabove, the method for preparing an oligomer and the apparatus for preparing oligomer according to the present invention have been described and illustrated in the drawings, but the description and the illustration in the drawings are the description and the illustration of only core constitutions for understanding of the present invention, and in addition to the process and apparatus described above and illustrated in the drawings, the process and the apparatus which are not described and illustrated separately may be appropriately applied and used for carrying out the method for preparing an oligomer and the apparatus for preparing oligomer according to the present invention.

Hereinafter, the present invention will be described in more detail by the Examples. However, the following Examples are provided for illustrating the present invention. It is apparent to a person skilled in the art that various modifications and alterations may be made without departing from the scope and spirit of the present invention, and the scope of the present invention is not limited thereto.

EXAMPLES

Example 1

Figure 1:
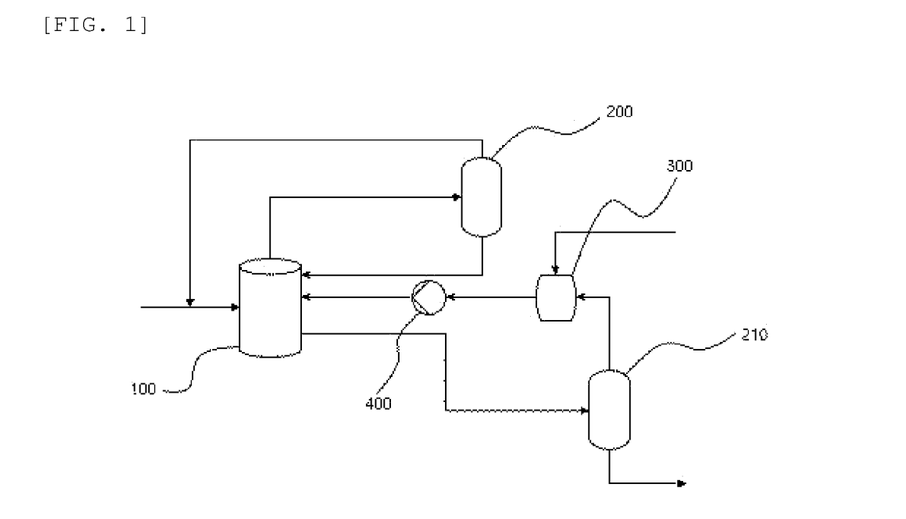
FIGS. 1 and 2 are process flowcharts of a method for preparing an oligomer according to an exemplary embodiment of the present invention, respectively.

For the process flowchart illustrated in FIG. 1, the process was simulated using an Aspen Plus simulator from Aspen Technology, Inc. Here, ethylene (C2) as the monomer was supplied to the reactor 100 at a reaction amount of 7,000 kg/hr or more, reaction conditions of the reactor 100 were set to a temperature of 90° C. and a pressure of 25 bar, methylcyclohexane was used as the solvent, and an amount of the solvent supplied was an equivalent amount to the sum of the product and the by-product in the second discharge stream supplied to the second separation device 210 in the reactor 100. The results are shown in the following Table 1.

TABLE 1

|  | Stream 1 | Stream 2 | Stream 3 | Stream 4 | Stream 5 |
| --- | --- | --- | --- | --- | --- |
| Phase | Liquid | Gaseous | Liquid | Liquid | Liquid |
| Temperature (° C.) | 90 | 2 | 30 | 10 | 11 |
| Pressure (bar) | 25 | 20 | 25 | 20 | 25 |
| Total flow rate (kg/hr) | 15,107 | 1,113 | 7,000 | 8,113 | 8,113 |
| Lights (kg/hr) | 218 | 167 | 0 | 167 | 167 |
| Ethylene (kg/hr) | 946 | 946 | 0 | 946 | 946 |
| Product (kg/hr) | 6,741 | 0 | 0 | 0 | 0 |
| Solvent (kg/hr) | 6,999 | 0 | 7,000 | 7,000 | 7,000 |
| Heavy (kg/hr) | 203 | 0 | 0 | 0 | 0 |

* Lights: a substance having a lower molecular weight than hexene among ethylene impurities and by-products
* Heavy: a substance having a higher molecular weight than octene among the by-products
* Product: a mixture of hexene and octene
* Stream 1: the second discharge stream from the reactor 100 which was supplied from the reactor 100 to the second separation device 210
* Stream 2: the upper discharge stream from the second separation device 210 which was supplied from the second separation device 210 to the monomer dissolution device 300
* Stream 3: the solvent stream which was supplied to the monomer dissolution device 300
* Stream 4: the discharge stream from the monomer dissolution device 300 which was supplied from the monomer dissolution device 300 by the pump 400
* Stream 5: the stream which was supplied from the pump 400 to the reactor 100

Referring to Table 1, it was confirmed in Stream 4 that ethylene recovered as Stream 3 was dissolved at a dissolution rate of 100%, and at this time, the temperature at which recovered ethylene is dissolved in the solvent in the monomer dissolution device 300 and discharged was 10° C., and it was confirmed therefrom that the cooling temperature of the recovered ethylene was significantly higher than the conventional temperature of −25° C. In addition, the pressure of Stream 4 was 20 bar, and the pressure of Stream 5 after passing through the pump 400 was 25 bar, from which it was found that the pressure was increased to the same pressure as the reactor 100.

Example 2

The process was performed in the same manner as in Example 1, except that methylcyclohexane was used as a first solvent and decane was used as a second solvent to simulate the process. Here, the first solvent was introduced at an equivalent amount to the sum of the product and the by-product, and the second solvent was introduced 0.5 times the sum of the product and the by-product. The results are shown in the following Table 2.

TABLE 2

|  | Stream 1 | Stream 2 | Stream 3 | Stream 4 | Stream 5 |
| --- | --- | --- | --- | --- | --- |
| Phase | Liquid | Gaseous | Liquid | Liquid | Liquid |
| Temperature (° C.) | 90 | 2 | 30 | 23 | 23 |
| Pressure (bar) | 25 | 20 | 25 | 20 | 25 |
| Total flow rate (kg/hr) | 18,344 | 1,350 | 10,000 | 11,350 | 11,350 |
| Lights (kg/hr) | 253 | 202 | 0 | 202 | 202 |
| Ethylene (kg/hr) | 1,147 | 1,147 | 0 | 1,147 | 1,147 |
| Product (kg/hr) | 6,741 | 0 | 0 | 0 | 0 |
| Solvent 1 (kg/hr) | 6,999 | 0 | 7,000 | 7,000 | 7,000 |
| Solvent 2 (kg/hr) | 3,000 | 0 | 3,000 | 3,000 | 3,000 |
| Heavy (kg/hr) | 203 | 0 | 0 | 0 | 0 |

* Lights: a substance having a lower molecular weight than hexene among ethylene impurities and by-products
* Heavy: a substance having a higher molecular weight than octene among the by-products
* Product: a mixture of hexene and octene
* Stream 1: the second discharge stream from the reactor 100 which was supplied from the reactor 100 to the second separation device 210
* Stream 2: the upper discharge stream from the second separation device 210 which was supplied from the second separation device 210 to the monomer dissolution device 300
* Stream 3: the solvent stream which was supplied to the monomer dissolution device 300
* Stream 4: the discharge stream from the monomer dissolution device 300 which was supplied from the monomer dissolution device 300 by the pump 400
* Stream 5: the stream which was supplied from the pump 400 to the reactor 100

Referring to Table 2, when two solvents were used, ethylene recovered as Stream 3 was dissolved at a dissolution rate of 100% in Stream 4, as compared with Example 1. In addition, the temperature at which the recovered ethylene is dissolved in the solvent in the monomer dissolution device 300 and discharged was 23° C., and it was found that the recovered ethylene monomer may be liquefied at a higher temperature than the temperature in the case of using one solvent at 23° C.

Example 3

Figure 2:
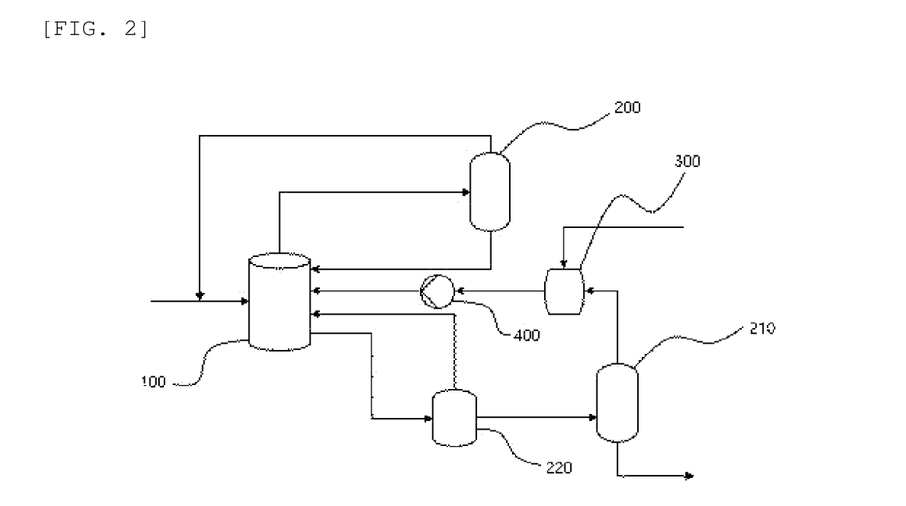

For the process flowchart illustrated in FIG. 2, the process was simulated using an Aspen Plus simulator from Aspen Technology, Inc. Here, ethylene (C2) as the monomer was supplied to the reactor 100 at a reaction amount of 7,000 kg/hr or more, the reaction conditions of the reactor 100 were set to a temperature of 90° C. and a pressure of 25 bar, methylcyclohexane was used as the solvent, and an amount of the solvent supplied was an equivalent amount to the sum of the product and the by-product in the second discharge stream supplied to the second separation device 210 in the reactor 100. The results are shown in the following Table 3.

TABLE 3

| | Stream 1-1 | Stream 1-2 | Stream 1-3 | Stream 2 | Stream 3 | Stream 4 | Stream 5 |
|---|---|---|---|---|---|---|---|
| Phase | Liquid | Gaseous | Liquid | Gaseous | Liquid | Liquid | Liquid |
| Temperature (° C.) | 90 | 120 | 120 | 2 | 30 | 23 | 23 |
| Pressure (bar) | 25 | 25 | 25 | 20 | 25 | 20 | 25 |
| Total flow rate (kg/hr) | 15207 | 333 | 14875 | 880 | 7000 | 7880 | 7880 |
| Lights (kg/hr) | 200 | 17 | 183 | 132 | 0 | 132 | 132 |
| Ethylene (kg/hr) | 954 | 206 | 748 | 748 | 0 | 748 | 748 |
| Product (kg/hr) | 6805 | 64 | 6741 | 0 | 0 | 0 | 0 |
| Solvent 1 (kg/hr) | 7045 | 45 | 6999 | 0 | 7000 | 7000 | 7000 |
| Heavy (kg/hr) | 204 | 0 | 203 | 0 | 0 | 0 | 0 |

\* Lights: a substance having a lower molecular weight than hexene among ethylene impurities and by-products
\* Heavy: a substance having a higher molecular weight than octene among the by-products
\* Product: a mixture of hexene and octene
\* Stream 1-1: the second discharge stream from the reactor 100 which was supplied from the reactor 100 to the third separation device 220.
\* Stream 1-2: the upper discharge stream from the third separation device 220 which was supplied from the third separation device 220 to the reactor 100.
\* Stream 1-3: the lower discharge stream from the third separation device 220 which was supplied from the third separation device 220 to the second separation device 210.
\* Stream 2: the upper discharge stream from the second separation device 210 which was supplied from the second separation device 210 to the monomer dissolution device 300.
\* Stream 3: the solvent stream which was supplied to the monomer dissolution device 300
\* Stream 4: the discharge stream from the monomer dissolution device 300 which was supplied from the monomer dissolution device 300 by the pump 400
\* Stream 5: the stream which was supplied from the pump 400 to the reactor 100

It was confirmed from Table 3 that in Stream 4, ethylene recovered as Stream 3 was dissolved at a dissolution rate of 100%. In addition, as compared with Example 1, the third separation device 220 was further installed between the reactor 100 and the second separation device 210 to partially recover the ethylene monomer primarily in the reactor 100, thereby decreasing the amount of the recovered ethylene monomer supplied to the monomer dissolution device 30 and liquefying the ethylene monomer at a higher temperature of 23° C.

COMPARATIVE EXAMPLES

Comparative Example 1

Figure 3:
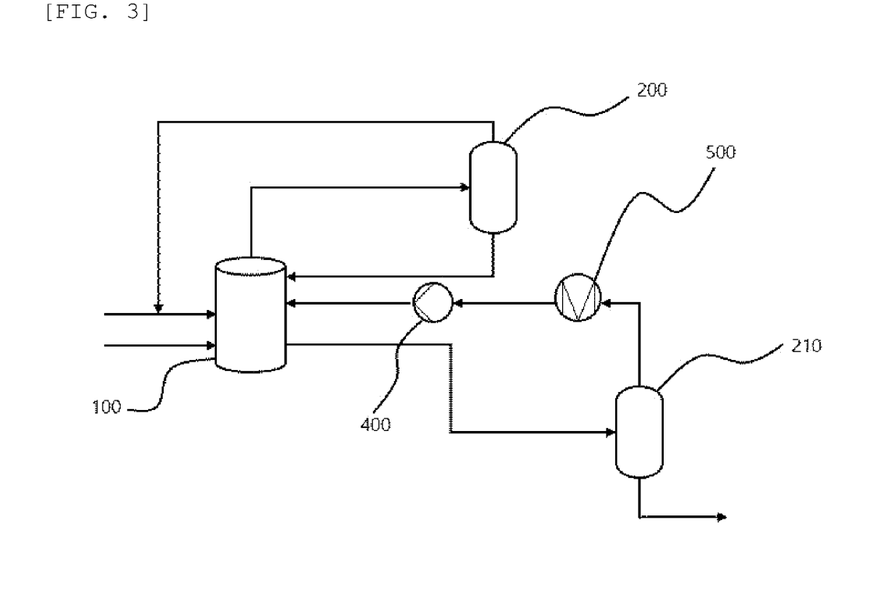
FIGS. 3 and 4 are process flowcharts of a method for preparing an oligomer according to Comparative Examples.

For the process flowchart illustrated in FIG. 3, the process was simulated using an Aspen Plus simulator from Aspen Technology, Inc. Here, ethylene (C2) as the monomer was supplied to the reactor 100 at a reaction amount of 7,000 kg/hr or more, the reaction conditions of the reactor 100 were set to a temperature of 90° C. and a pressure of 25 bar, methylcyclohexane was used as the solvent supplied to the reactor 100, and an amount of the solvent supplied was an equivalent amount to the sum of the product and the by-product in the second discharge stream supplied to the second separation device 210 in the reactor 100. The results are shown in the following Table 4.

TABLE 4

| | Stream 1 | Stream 2-1 | Stream 3-1 | Stream 4-1 | Stream 5 |
|---|---|---|---|---|---|
| Phase | Liquid | Gaseous | Liquid | Liquid | Liquid |
| Temperature (° C.) | 90 | 11 | 30 | −26 | −25 |
| Pressure (bar) | 25 | 20 | 25 | 20 | 25 |
| Total flow rate (kg/hr) | 15,183 | 1,188 | 7,000 | 1,188 | 1,188 |
| Lights (kg/hr) | 288 | 237 | 0 | 237 | 237 |
| Ethylene (kg/hr) | 951 | 951 | 0 | 951 | 951 |
| Product (kg/hr) | 6,741 | 0 | 0 | 0 | 0 |
| Solvent (kg/hr) | 6,999 | 0 | 7,000 | 0 | 0 |
| Heavy (kg/hr) | 203 | 0 | 0 | 0 | 0 |

\* Lights: a substance having a lower molecular weight than hexene among ethylene impurities and by-products
\* Heavy: a substance having a higher molecular weight than octene among the by-products
\* Product: a mixture of 1-nexene and 1-octene.
\* Stream 1: the second discharge stream from the reactor 100 which was supplied from the reactor 100 to the second separation device 210.
\* Stream 2-1: the upper discharge stream from the second separation device 210 which was supplied from the second separation device 210 to a condenser 500.
\* Stream 3-1: the solvent scream which was supplied to the reactor 100
\* Stream 4-1: the discharge stream from the condenser 500 which was supplied from the condenser 500 by the pump 400
\* Stream 5: the stream supplied from the pump 400 to the reactor 100

Referring to Table 4, in order to increase the pressure of Stream 2-1 including the recovered gaseous ethylene monomer to the pressure of the reactor 100 using the pump 400, the stream should be a liquid phase. To this end, the condenser 500 is needed, and it was found from Stream 4-1 which is a stream including a condensed ethylene monomer in the condenser 500 that Stream 4-1 was at a temperature of −26° C., which is a significantly low temperature as compared with Examples 1 to 3.

Comparative Example 2

Figure 4:
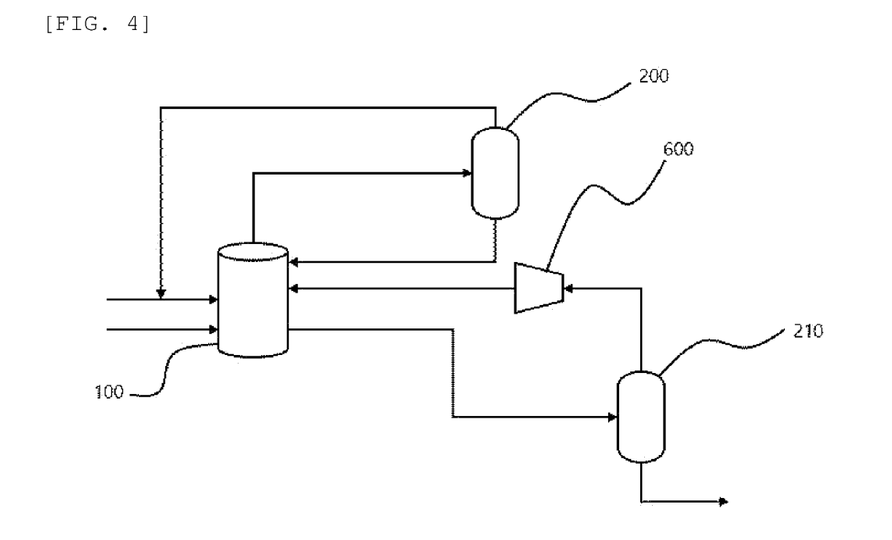

For the process flowchart illustrated in FIG. 4, the process was simulated using an Aspen Plus simulator from Aspen Technology, Inc. Here, ethylene (C2) as the monomer was supplied to the reactor 100 at a reaction amount of 7,000 kg/hr or more, the reaction conditions of the reactor 100 were set to a temperature of 90° C. and a pressure of 25 bar, methylcyclohexane was used as the solvent supplied to the reactor, and the amount of the solvent supplied was an equivalent amount to the sum of the product and the by-product in the second discharge stream supplied to the second separation device 210 in the reactor 100. The results are shown in the following Table 5.

TABLE 5

| | Stream 1 | Stream 2-2 | Stream 3-1 | Stream 4-2 |
|---|---|---|---|---|
| Phase | Liquid | Gaseous | Liquid | Gaseous |
| Temperature (° C.) | 90 | 11 | 30 | 28 |
| Pressure (bar) | 25 | 20 | 25 | 25 |
| Total flow rate (kg/hr) | 15,183 | 1,188 | 7,000 | 1,188 |
| Lights (kg/hr) | 288 | 237 | 0 | 237 |
| Ethylene (kg/hr) | 951 | 951 | 0 | 951 |
| Product (kg/hr) | 6,742 | 0 | 0 | 0 |
| Solvent (kg/hr) | 7,000 | 0 | 7,000 | 0 |
| Heavy (kg/hr) | 203 | 0 | 0 | 0 |

\* Lights: a substance having a lower molecular weight than hexene among ethylene impurities and by-products
\* Heavy: a substance having a higher molecular weight than octene
\* Product: a mixture of hexene and octene
\* Stream 1: the second discharge stream from the reactor 100 which was supplied from the reactor 100 to the second separation device 210
\* Stream 2-2: the upper discharge stream from the second separation device 210 which was supplied from the second separation device 210 to a compressor 600.
\* Stream 3-1: the solvent stream which was supplied to the reactor 100
\* Stream 4-2: the stream which was supplied from the compressor 600 to the reactor 100

Referring to Table 5, in order to supply the gaseous ethylene monomer recovered in the second separation device 210 to the reactor 100, it was found that the compressor 600 was separately installed for increasing the pressure. In this case, the process was economically infeasible due to increased investment costs.

The invention claimed is:

1. A method for preparing an oligomer, the method comprising:
    supplying a feed stream including a monomer to a reactor and performing an oligomerization reaction;
    supplying a first discharge stream from the reactor to a first separation device and supplying a second discharge stream from the reactor to a second separation device;
    recovering the monomer in the second separation device as an upper discharge stream;
    supplying the upper discharge stream including the monomer from the second separation device to a monomer dissolution device to dissolve the upper discharge stream in a solvent supplied to the monomer dissolution device; and
    supplying a discharge stream from the monomer dissolution device to the reactor,
    wherein the discharge stream from the monomer dissolution device is a liquid stream including the monomer dissolved in the solvent.

2. The method for preparing an oligomer of claim 1, wherein the upper discharge stream from the second separation device is a gaseous stream.

3. The method for preparing an oligomer of claim 1, wherein the solvent is one or more selected from the group consisting of n-pentane, n-hexane, n-heptane, cyclohexane, methylcyclohexane, octane, cyclooctane, decane, dodecane, benzene, xylene, 1,3,5-trimethylbenzene, toluene, ethylbenzene, chlorobenzene, dichlorobenzene, and trichlorobenzene.

4. The method for preparing an oligomer of claim 1, wherein a temperature of the discharge stream from the monomer dissolution device is in a range of −10° C. to 50° C.

5. The method for preparing an oligomer of claim 1, wherein a pressure of the discharge stream from the monomer dissolution device is in a range of 10 bar to 45 bar.

6. The method for preparing an oligomer of claim 1, wherein the following General Formula 1 is satisfied:

$(M2/M1) \times 100 \geq 80$ weight percent(wt %)     [General Formula 1]

wherein M1 is a content of the monomer in the upper discharge stream from the second separation device, and M2 is a content of the monomer in the discharge stream from the monomer dissolution device.

7. The method for preparing an oligomer of claim 1, wherein the monomer is ethylene and the oligomer is an alpha-olefin.

8. The method for preparing an oligomer of claim 1, wherein an upper discharge stream and a lower discharge stream from the first separation device is supplied to the reactor.

9. An apparatus for preparing oligomer comprising:
    a reactor for oligomerizing a feed stream including a monomer, supplying a first discharge stream to a first separation device, and supplying a second discharge stream to a second separation device;
    a first separation device for being supplied with the first discharge stream from the reactor;
    a second separation device for being supplied with the second discharge stream from the reactor and supplying an upper discharge stream to a monomer dissolution device; and
    a monomer dissolution device for dissolving the upper discharge stream from the second separation device in a solvent and supplying a discharge stream to the reactor,
    wherein the discharge stream from the monomer dissolution device is a liquid stream including the monomer dissolved in the solvent.

10. A method for preparing an oligomer, the method comprising:
    supplying a feed stream including a monomer to a reactor and performing an oligomerization reaction;
    supplying a first discharge stream from the reactor to a first separation device and supplying a second discharge stream from the reactor to a third separation device;
    supplying an upper discharge stream from the third separation device to the reactor, and supplying a lower discharge stream from the third separation device to the second separation device;
    recovering the monomer in the second separation device as an upper discharge stream;

supplying the upper discharge stream including the monomer from the second separation device to a monomer dissolution device to dissolve the upper discharge stream in a solvent supplied to the monomer dissolution device; and supplying a discharge stream from the monomer dissolution device to the reactor, wherein the discharge stream from the monomer dissolution device is a liquid stream including the monomer dissolved in the solvent.

11. An apparatus for preparing oligomer comprising:

a reactor for oligomerizing a feed stream including a monomer, supplying a first discharge stream to a first separation device, and supplying a second discharge stream to a second separation device;

a first separation device for being supplied with the first discharge stream from the reactor;

a third separation device for being supplied with the second discharge stream from the reactor and supplying a lower discharge stream to the second separation device;

a second separation device for being supplied with the lower discharge stream from the third separation device and supplying an upper discharge stream to a monomer dissolution device; and a monomer dissolution device for dissolving the upper discharge stream from the second separation device in a solvent and supplying a discharge stream to the reactor, wherein the discharge stream from the monomer dissolution device is a liquid stream including the monomer dissolved in the solvent.

* * * * *